(12) United States Patent
Kelkenberg et al.

(10) Patent No.: US 12,419,518 B2
(45) Date of Patent: Sep. 23, 2025

(54) OPHTHALMIC INSTRUMENT PROBE DETECTION METHOD

(71) Applicant: REICHERT, INC., Depew, NY (US)

(72) Inventors: David G. Kelkenberg, Akron, NY (US); John W. Taylor, Cowlesville, NY (US); Eric V. Palmer, Lancaster, NY (US); David J. Cash, Depew, NY (US)

(73) Assignee: REICHERT, INC., Depew, NY (US)

( * ) Notice: Subject to any disclaimer, the term of this patent is extended or adjusted under 35 U.S.C. 154(b) by 275 days.

(21) Appl. No.: 18/234,484

(22) Filed: Aug. 16, 2023

(65) Prior Publication Data
US 2025/0060500 A1 Feb. 20, 2025

(51) Int. Cl.
A61B 3/16 (2006.01)
G01L 9/00 (2006.01)
G01L 9/10 (2006.01)
G01V 3/02 (2006.01)

(52) U.S. Cl.
CPC ............ A61B 3/16 (2013.01); G01L 9/0029 (2013.01); G01L 9/0089 (2013.01); G01L 9/10 (2013.01); G01V 3/02 (2013.01)

(58) Field of Classification Search
CPC ........... A61B 3/10; A61B 3/16; G01L 9/0026; G01L 9/0029; G01L 9/0089; G01L 9/10
See application file for complete search history.

(56) References Cited

U.S. PATENT DOCUMENTS

| 5,198,764 | A | 3/1993 | Spencer |
| 5,355,884 | A | 10/1994 | Bennett |
| 6,093,147 | A | 7/2000 | Kontiola |
| 8,998,810 | B2 | 4/2015 | Kontiola |
| 11,026,577 | B2 | 6/2021 | Martin |
| 11,717,162 | B2 | 8/2023 | Martin |
| 2005/0137473 | A1 | 6/2005 | Kontiola |
| 2005/0137474 | A1 | 6/2005 | Kontiola |
| 2008/0103381 | A1* | 5/2008 | Kontiola .................. A61B 3/16 600/405 |
| 2018/0368681 | A1 | 12/2018 | Makkeli et al. |
| 2019/0380577 | A1 | 12/2019 | Martin |
| 2021/0235988 | A1 | 8/2021 | Parks et al. |

(Continued)

FOREIGN PATENT DOCUMENTS

| CN | 219126311 U | * | 6/2023 |
| FI | 129681 B | | 6/2022 |
| FI | 129790 B | | 8/2022 |

(Continued)

Primary Examiner — Douglas X Rodriguez
Assistant Examiner — Kendrick X Liu
(74) Attorney, Agent, or Firm — Hodgson Russ LLP

(57) ABSTRACT

A method of detecting presence or absence of a magnetic measurement probe at a measurement launch position in an electromagnetic coil of an ophthalmic instrument includes applying a temporary current pulse to the electromagnetic coil, detecting a counter-electromotive force voltage spike induced in the electromagnetic coil by the current pulse, evaluating a decay behavior of the counter-electromotive force voltage spike, and correlating the decay behavior of the counter-electromotive force voltage spike to presence or absence of the measurement probe at the measurement launch position.

18 Claims, 5 Drawing Sheets

(56) References Cited

U.S. PATENT DOCUMENTS

2022/0409044 A1    12/2022  Salkola
2024/0315557 A1*   9/2024   Ehnholm ................. A61B 3/16

FOREIGN PATENT DOCUMENTS

| FI | 130061 B | 1/2023 |
|---|---|---|
| WO | 2023012402 A1 | 2/2023 |
| WO | 2023067241 A1 | 4/2023 |

* cited by examiner

OPHTHALMIC INSTRUMENT PROBE DETECTION METHOD

FIELD OF THE DISCLOSURE

The present disclosure relates to ophthalmic instruments for measuring properties of an eye by propelling a disposable probe into momentary contact with the eye. One example of such an ophthalmic instrument is a rebound tonometer for measuring intraocular pressure (IOP).

BACKGROUND OF THE DISCLOSURE

A rebound tonometer is an ophthalmic instrument that propels a movable measurement probe in a controlled manner toward the cornea of an eye to measure IOP. The measurement probe is a disposable item typically having an elongated shaft terminating in a rounded tip. A new sterile measurement probe is loaded in the rebound tonometer prior to taking measurements on a test subject. During a measurement, the probe contacts the cornea, is decelerated at a rate which depends on intraocular pressure, and then rebounds in a direction away from the cornea back toward the instrument housing. The rebound tonometer detects the motion of the measurement probe and determines intraocular pressure based on a measurement signal representing detected motion of the probe. In some cases, the instrument may also determine parameters related to corneal biomechanics based on the measurement signal.

In known rebound tonometers, a pair of axially aligned electromagnetic coils may be arranged in the instrument housing, and the measurement probe may have a magnetized shaft which extends through an opening in the housing for receipt within a core passageway of each coil. A rear coil of the pair may be energized to retain the probe in a launch position in the instrument before measurement takes place. A front coil of the pair located between the rear coil and the opening in the housing may be energized momentarily, and the rear coil de-energized, to propel the probe toward the cornea by electromotive force. After energizing current to the front coil is shut off, a current may be induced in the rear coil by the moving probe shaft to provide a detectable voltage signal (a measurement signal) representing motion of the probe. After measurements have been taken on a test subject, the used measurement probe is discarded.

Before a measurement cycle is commenced, it is helpful for the instrument to detect whether or not a probe is loaded and present in a suitable launch position. If not, the instrument may be programmed to assist the operator to ensure a probe is properly loaded. Knowing if a probe is present is an important piece of information which affects workflow and the ability of the instrument to assist the operator. One known method of detecting presence of a probe is to put the probe into motion by briefly energizing the front coil to move the probe a short distance, and detecting the motion by monitoring current induced in the rear coil, whereby probe presence is indicated in the form of a probe velocity measurement signal. This is not ideal because it consumes significant energy. Also, if a probe is present but is stuck or jammed, the prior art detection method incorrectly determines that a probe is not present because no motion of the probe is detected.

SUMMARY OF THE DISCLOSURE

An ophthalmic instrument probe detection method of the present disclosure has low-energy consumption, does not affect the normal measurement operation process of the instrument, and provides an opportunity to determine if a probe is present but stuck or jammed in the instrument.

In an embodiment of the present disclosure, a method of detecting presence or absence of a measurement probe at a measurement launch position in an ophthalmic instrument is provided. The measurement probe has an elongated magnetic shaft, and the ophthalmic instrument includes an electromagnetic coil defining a core passageway for receiving at least a portion of the magnetic shaft when the magnetic shaft is at the measurement launch position. The method comprises the steps of applying a temporary current pulse to the electromagnetic coil, detecting a counter-electromotive force (i.e., "back EMF") voltage spike induced in the electromagnetic coil by the current pulse, evaluating a decay behavior of the counter-electromotive force voltage spike, and correlating the decay behavior of the counter-electromotive force voltage spike to presence or absence of the measurement probe at the measurement launch position.

In one implementation, evaluating the decay behavior of the counter-electromotive force voltage spike includes calculating a decay score corresponding to a summation of sampled signal amplitudes of the counter-electromotive force voltage spike acquired over a predetermined period of time. The decay behavior of the counter-electromotive force voltage spike may be correlated to presence of the measurement probe at the measurement launch position when the decay score is greater than a predetermined decay score threshold, and the decay behavior of the counter-electromotive force voltage spike may be correlated to absence of the measurement probe at the measurement launch position when the decay score is less than or equal to the predetermined decay score threshold. The predetermined decay score threshold may be determined during calibration of the ophthalmic instrument and stored in instrument memory.

In another implementation, evaluating the decay behavior of the counter-electromotive force voltage spike includes measuring a decay time of the counter-electromotive force voltage spike. The decay behavior of the counter-electromotive force voltage spike may be correlated to presence of the measurement probe at the measurement launch position when the decay time is greater than a predetermined decay time threshold, and the decay behavior of the counter-electromotive force voltage spike may be correlated to absence of the measurement probe at the measurement launch position when the decay time is less than or equal to the predetermined decay score threshold. The predetermined decay time threshold may be determined during calibration of the ophthalmic instrument and stored in instrument memory.

If the disclosed method determines that a probe is present in the launch position, the measurement system may be enabled to commence a measurement cycle by energizing a coil of the instrument (e.g., either the mentioned electromagnetic coil or another coil) to launch the probe toward the eye, and a voltage induced in the electromagnetic coil may be monitored to detect motion of the probe. If no motion of the probe is detected, then an error message may be displayed to inform the operator that the probe is stuck or jammed in the instrument and cannot move.

The present disclosure extends to an ophthalmic instrument configured to use the probe detection method summarized above. In one embodiment, the ophthalmic instrument comprises an electromagnetic coil defining a core passageway, drive electronics configured to connect a first voltage to the electromagnetic coil to apply a temporary current pulse in the electromagnetic coil, measurement electronics configured to detect a counter-electromotive force voltage spike induced in the electromagnetic coil by the current pulse and generate a probe detection signal representing the counter-electromotive force voltage spike, and processing electronics configured to evaluate a decay behavior of the counter-electromotive force voltage spike and correlate the decay behavior of the counter-electromotive force voltage spike to presence or absence of a disposable measurement probe at a measurement launch position within the core passageway.

The drive electronics may be further configured to energize the electromagnetic coil to retain the measurement probe at the measurement launch position if the measurement probe is found to be present at the measurement launch position. In one implementation, the drive electronics may be configured to connect a second voltage to the electromagnetic coil to energize the electromagnetic coil to retain the measurement probe at the measurement launch position, wherein the second voltage is greater than the first voltage.

BRIEF DESCRIPTION OF THE DRAWING VIEWS

The nature and mode of operation of the present disclosure will now be more fully described in the following detailed description taken with the accompanying drawing figures, in which.

DETAILED DESCRIPTION OF THE DISCLOSURE

Figures 1, 2:
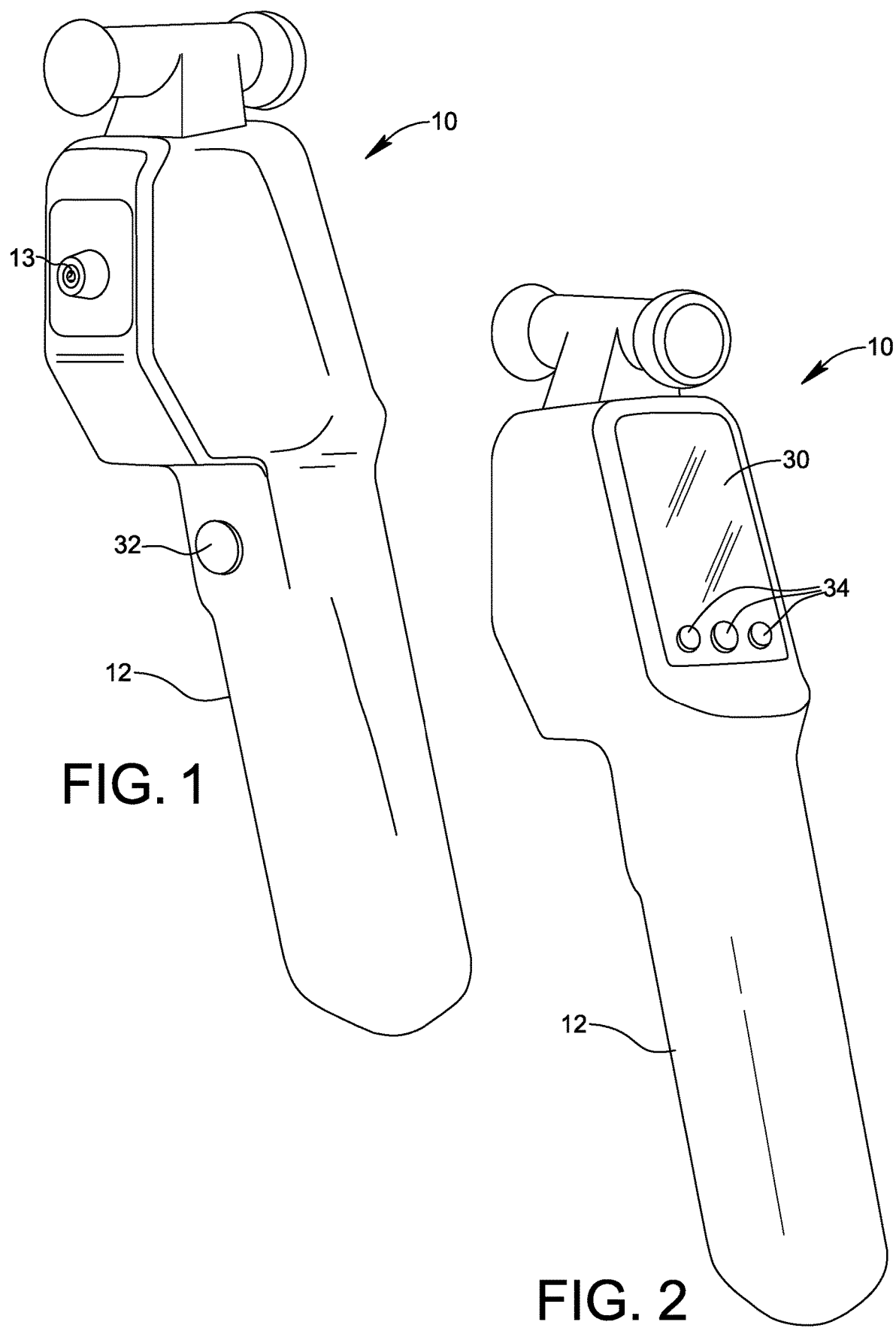
FIG. 1 is a perspective view of an ophthalmic instrument formed in accordance with an embodiment of the present disclosure.
FIG. 2 is another perspective view of an ophthalmic instrument formed in accordance with an embodiment of the present disclosure.
Figure 3:
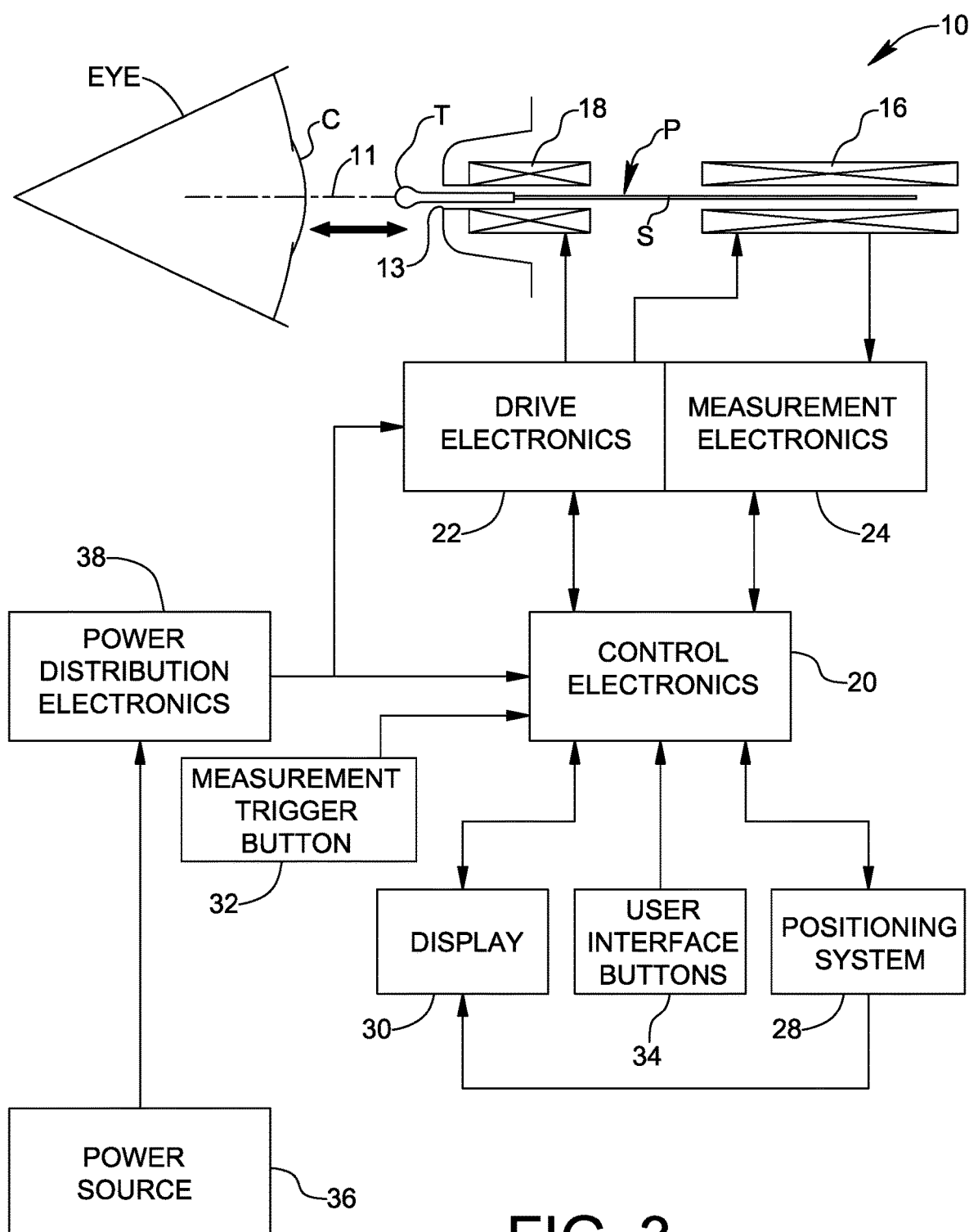
FIG. 3 is a schematic block diagram of the ophthalmic instrument shown in FIGS. 1 and 2.

FIGS. 1 and 2 show an ophthalmic instrument 10 formed in accordance with an embodiment of the present disclosure, and FIG. 3 schematically illustrates ophthalmic instrument 10. In the present disclosure, ophthalmic instrument 10 is embodied as a rebound tonometer configured to measure IOP. However, ophthalmic instrument 10 may be configured to measure other properties of the eye, for example biomechanical characteristics of the corneal tissue. Ophthalmic instrument 10 generally comprises a hand-held housing 12 supporting a measurement system configured to propel a disposable measurement probe P in a forward direction (right to left in FIG. 3) along a measurement axis 11 toward an eye of test subject, wherein probe P contacts a cornea C of the eye and is rebounded from the cornea in a reverse direction opposite the forward direction.

For sake of the present disclosure and claims, disposable probe P is not considered to be a structural component of ophthalmic instrument 10, it is considered to be a "work piece" acted upon by ophthalmic instrument 10. Probe P may include an elongated shaft S, at least a portion of which is made of a magnetic material, and a rounded tip T at an end of shaft S for contacting cornea C.

The measurement system of ophthalmic instrument 10 may include a rear electromagnetic coil 16 and a front electromagnetic coil 18. Front coil 18 may be axially aligned with rear coil 16 and situated between rear coil 16 and a probe opening 13 through a front surface of housing 12.

When probe P is loaded in ophthalmic instrument 10 at a suitable launch position as illustrated in FIG. 3, magnetic shaft S of probe P extends through probe opening 13, through a core passageway defined by front coil 18, and at least partially into a core passageway defined by rear coil 16. When probe P occupies a launch position as shown in FIG. 3, the tip T of probe P protrudes from opening 13 by a short distance.

The measurement system may include control electronics 20, drive electronics 22, and measurement electronics 24. Drive electronics 22 may be configured to apply a drive voltage to front coil 18 to energize the front coil to propel probe P forward toward the eye by electromotive force in the manner of a solenoid. Drive electronics 22 may also be configured to apply a drive voltage to rear coil 16 to energize the rear coil such that probe P is urged away from the eye and retained at a launch position in ophthalmic instrument 10 prior to a measurement cycle. Appropriate drive commands may be provided to drive electronics 22 by control electronics 20. As mentioned, rear coil 16 may be energized to retain probe P at a launch position prior to measurement. When measurement axis 11 of instrument 10 is properly aligned with cornea C for a measurement, rear coil 16 may be de-energized and front coil 18 energized to propel probe P toward the cornea for contact with and rebound from the corneal surface. The velocity of probe P may be detected using measurement electronics 24 to monitor a voltage induced in rear coil 16 by motion of magnetic probe shaft S. An analog voltage measurement signal from rear coil 16 representing velocity of probe P as a function of time may be amplified and filtered by measurement electronics 24 and converted to a digital signal by an analog-to-digital converter 26 (see FIG. 5) for processing by control electronics 20.

Control electronics 20 may comprise a microcontroller having on-board memory for storing programming instructions, for example software and firmware, that are executed by processing electronics of the microcontroller. Alternatively or additionally, control electronics 20 may comprise processing electronics including one or more microprocessors and external memory connected to the microprocessor(s) for storing programming instructions executed by the microprocessor(s). Control electronics 20 may be programmed to calculate a basic IOP measurement value from the digitized measurement signal representing probe velocity as a function of time. Alternatively or additionally, control electronics 20 may be programmed to calculate biomechanical characteristics of the corneal tissue from the digitized measurement signal. As may be understood, analog-to-digital converter 26 may be integrated with control electronics 20.

As is known in the art of ophthalmic instruments, the measurement system may further include an opto-electronic positioning system 28 and a display 30 configured to guide and confirm alignment of a measurement axis 11 with cornea C and positioning of a front surface of instrument 10 at a predetermined working distance from cornea C. A trigger button 32 may be provided on housing 12 for enabling an operator to send a signal to control electronics 20 to initiate a measurement cycle, and/or the positioning system 28 may automatically send a signal to control electronics 20 to initiate a measurement cycle when alignment and proper working distance are confirmed by the positioning system. Display 30 may also be used to selectively display operational menu choices and measurement information to an operator through one or more user interface buttons 34. Ophthalmic instrument 10 further comprises a power source 36, for example a rechargeable battery, and power distribution electronics 38.

Figure 4:
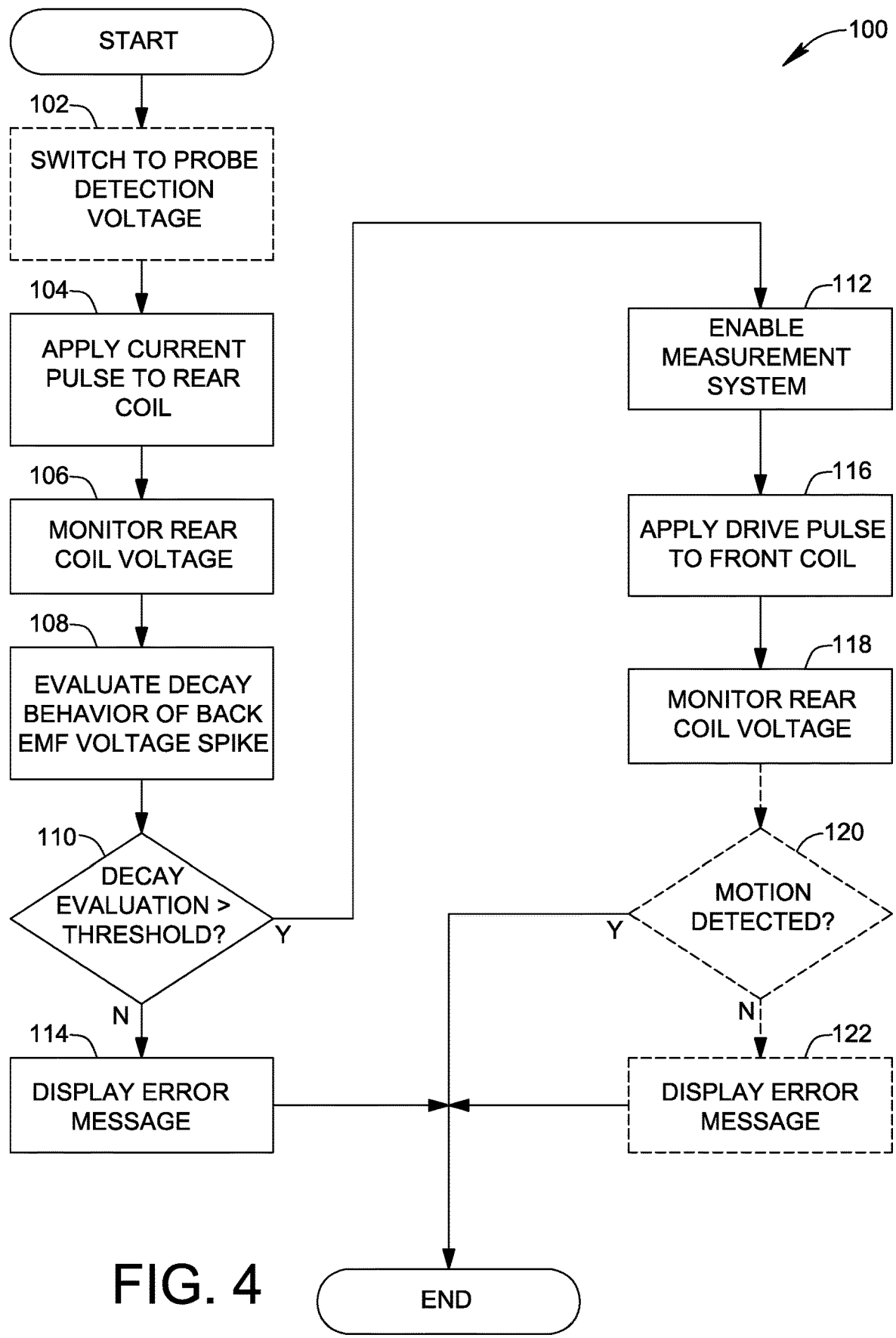
FIG. 4 is a flow diagram illustrating a probe detection method in accordance with an embodiment of the present disclosure.

Prior to executing a measurement cycle on a test subject, instrument 10 may execute a probe detection routine according to the present disclosure to confirm whether or not probe P is present in the launch position, i.e., to confirm whether or not a portion of magnetic shaft S is present within the core passageway defined by rear coil 16. Reference is made to FIG. 4 for describing an embodiment of the probe detection method generally identified by reference numeral 100.

Figure 5:
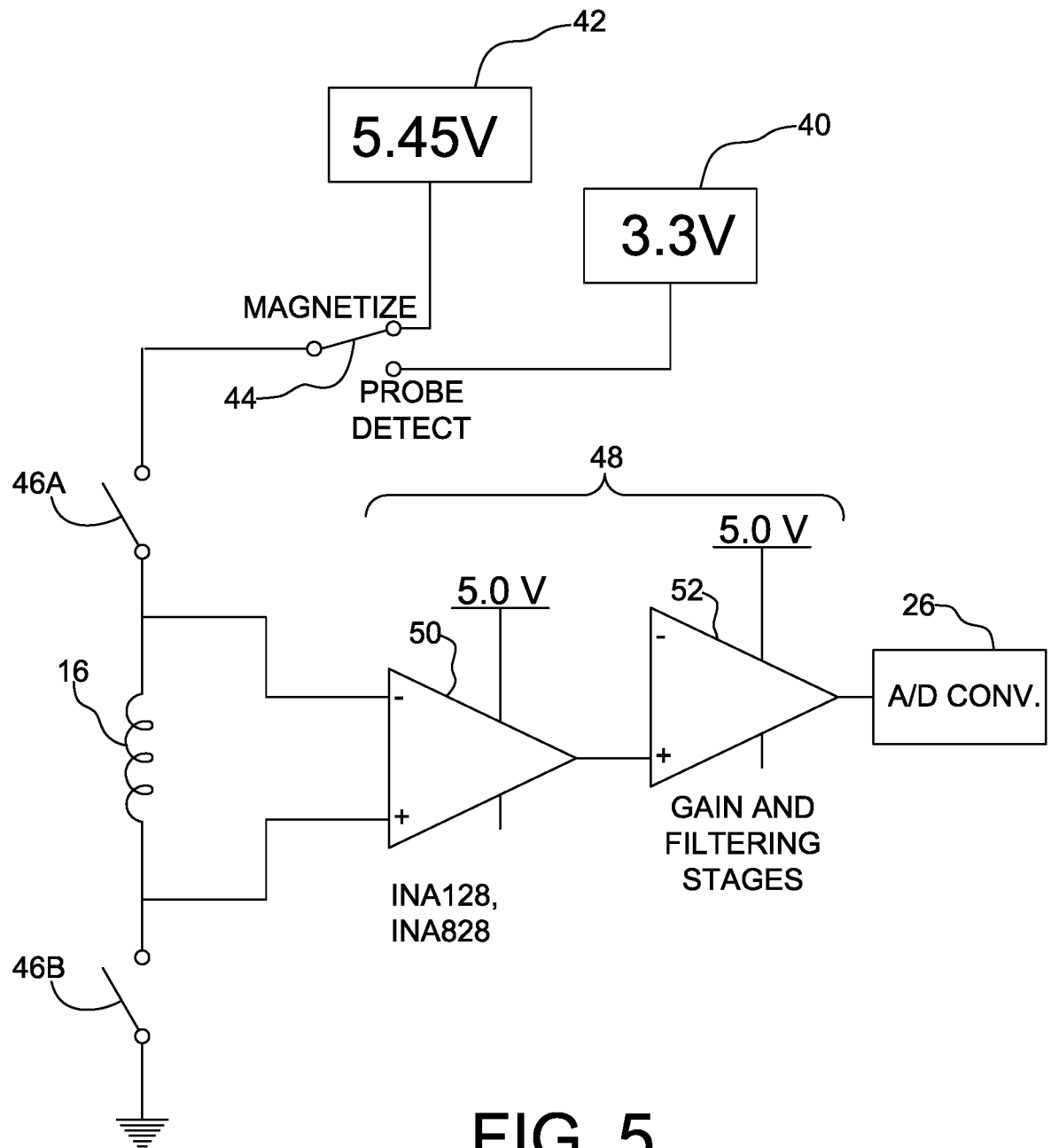
FIG. 5 is a high-level circuit diagram illustrating circuitry for energizing an electromagnetic coil of the ophthalmic instrument in accordance with an embodiment of the present disclosure.

Step 102 of method 100 is switching a supply voltage connectable to rear electromagnetic coil 16 from a measurement voltage level to a probe detection voltage level. This step may be omitted or made optional (as indicated by dotted lines) if instrument 10 defaults to the probe detection voltage level when the user is prompted to load a new measurement probe P, or if the probe detection voltage level is the same as the measurement voltage level. For reasons explained below, it may be advantageous to use a probe detection voltage level that is lower than the measurement voltage level. In one embodiment, the probe detection voltage level may be 3.3 V, and the measurement voltage level may be 5.45 V. Of course, other suitable voltages levels may be used. FIG. 5 is a simplified circuit diagram illustrating circuitry for energizing rear electromagnetic coil 16 in accordance with an embodiment of the present disclosure. Rear coil 16 has one end connectable to ground and a second end connectable to either a first voltage source 40 or a second voltage source 42 as determined by a voltage level selection switch 44. First voltage source 40 may be, for example, a 3.3 V source, and second voltage source 42 may be, for example, at 5.45 V source. In FIG. 5, a high side switch 46A is provided between rear coil 16 and voltage level selection switch 44, and a low side switch 46B is provided between rear coil 16 and ground. Switches 46A, 46B may be closed together in tandem to connect rear coil 16 to a selected voltage source 40 or 42, and switches 46A, 46B may be opened together in tandem to disconnect rear coil 16 from the selected voltage source.

Step 104 of method 100 is applying a temporary current pulse to electromagnetic coil 16. Control electronics 20 may be programmed by software or firmware to apply a brief current pulse to rear coil 16. For example, control electronics 20 may be programmed to send command signals to close switches 46A, 46B together in tandem and then reopen switches 46A, 46B together in tandem after a predetermined time period has elapsed, whereby a temporary current pulse is applied to rear coil 16. In an embodiment of the method, the voltage connected to electromagnetic coil 16 may be a first voltage corresponding to the probe detection voltage level. The voltage may be applied to coil 16 for a time period in a range of 1-3 milliseconds to generate a current pulse of the same duration. In one embodiment, the applied voltage for purposes of probe detection is 3.3 V. As explained below, a probe detection voltage other than 3.3 V may be used.

Step 106 of method 100 involves detecting a counter-electromotive force voltage spike induced in the electromagnetic coil 16 by the applied current pulse by monitoring the voltage across rear coil 16. Just after the falling edge of the current pulse, voltage across rear coil 16, acting as an inductor, is monitored. Counter-electromotive force voltage Γ1 (t) induced in coil 16 is given by the relationship $$V_L(t) = -L\frac{di}{dt}$$

where L is the self-inductance and di/dt is the rate of current change. As may be seen in FIG. 5, measurement electronics for monitoring voltage across rear coil 16 may include an amplification circuit 48 including a low power instrumentation amplifier 50 connected to gain and filtering electronics 52. Amplifier 50 may be, for example, an INA828 or INA128 instrumentation amplifier from Texas Instruments.

Implementation of step 106 is significantly complicated and almost rendered impossible by the signal levels involved. The amplification circuit 48 used to measure voltage induced in rear coil 16 by motion of probe P during a test subject measurement cycle typically has a gain of about 2370. For purposes of probe detection, a very large signal is applied (the probe detection pulse), which overloads the amplification circuit 48 and can prevent observation of the counter-electromotive force voltage spike. To address this problem, the inventors provided capability for switching between a lower supply voltage level (e.g., first voltage source 40) for probe detection and a higher supply voltage level (e.g., second voltage source 42) used by drive electronics 22 to energize front coil 18 to propel the probe P toward the eye during a test subject measurement cycle and to energize rear coil 16 to retain probe P in instrument 10 prior to a test subject measurement cycle. The capability to switch to a lower supply voltage level for probe detection helps solve the overload problem mentioned above.

As an alternative solution, amplification circuit 48 may use an amplifier designed to handle the overload condition, and switching to a lower probe detection voltage level may be avoided. However, such amplifiers are difficult to find, and successful operation typically relies on undocumented, untested features of the amplifier. The INA128 instrumentation amplifier from Texas Instruments, mentioned above, has an internal overvoltage protection diode with documented performance characteristics and is fast enough not to significantly obscure the counter-electromotive force voltage spike induced by the temporary current pulse, such that switching to a lower probe detection voltage level is unnecessary. By contrast, the overload protection characteristics of the mentioned INA828 instrumentation amplifier from Texas Instruments are undocumented and may obscure the counter-electromotive force voltage spike due to slow response, such that switching to a lower probe detection voltage level is recommended.

Another possible solution to the overload problem is to add completely different signal conditioning electronics with lower gain for the exclusive purpose of measuring the counter-electromotive force voltage spike. However, this solution is not preferred due to the increased expense involved. Another option for dealing with overload is to raise the supply voltage for the amplifiers in amplification circuit 48, however this is not preferred because of higher cost, increased power consumption, and difficulty sourcing suitable electronic components.

Figure 6:
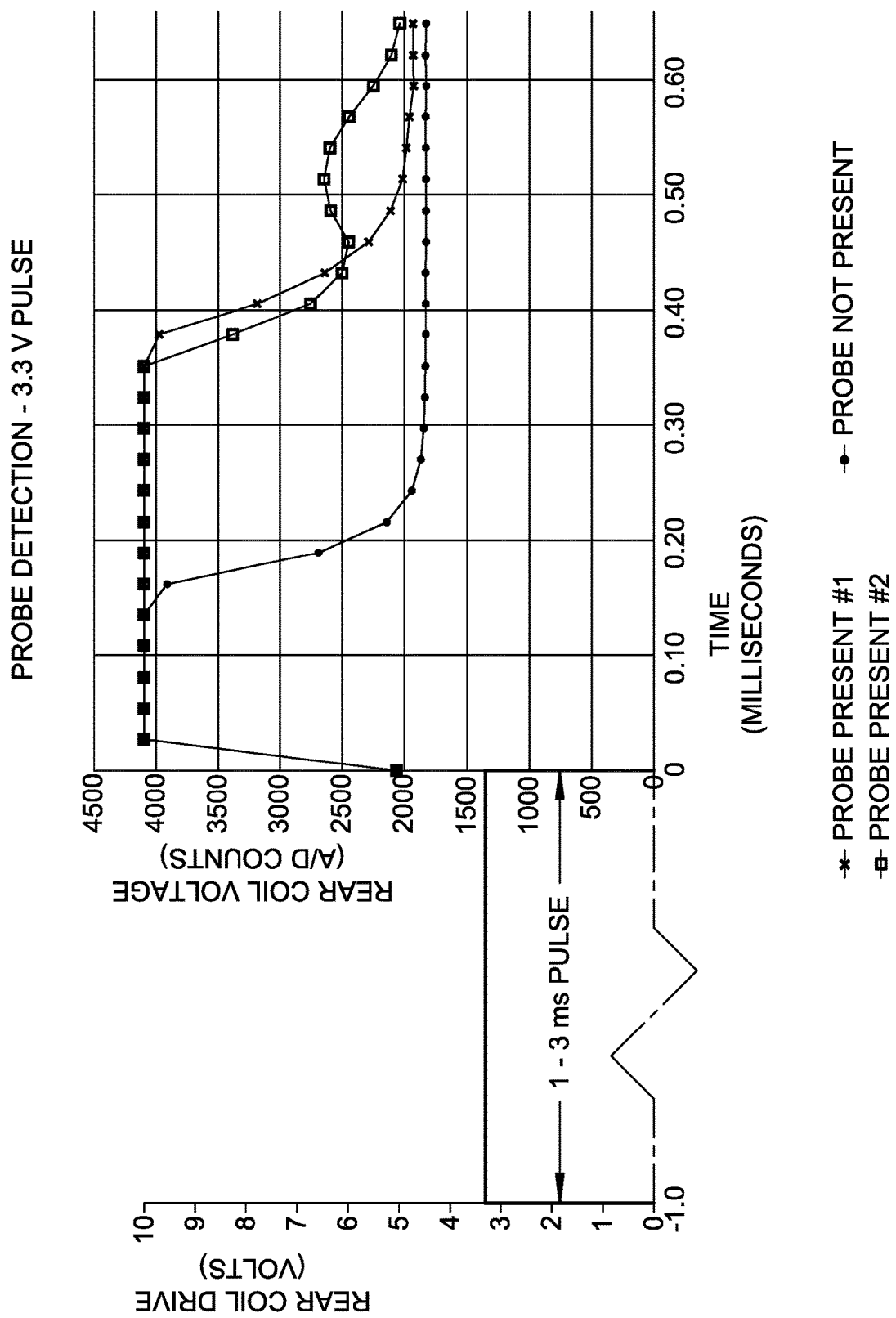
FIG. 6 is a graph plotting electromagnetic coil voltage versus time during a probe detection method of the present disclosure for a case where no probe is present and cases where a probe is present.

The voltage signal outputted by gain and filtering electronics 52 may be digitized by analog-to-digital converter 26 for evaluation by digital processing circuitry of control electronics 20. FIG. 6 illustrates typical counter-electromotive force voltage spikes detected for one case where probe P is not present at a launch position and two cases case where probe P is present at a launch position. As may be seen, voltage may be sampled at regular time intervals of about 0.027 milliseconds over a total time period of about 0.650 milliseconds, a time period that allows the voltage spike amplitude to decay to a baseline level. Voltage amplitude, expressed in digital counts, is plotted as a function of time. It is apparent from FIG. 6 that a period of time required for the counter-electromotive force voltage spike to decay from its peak amplitude to a lower amplitude (the "decay time" of the counter-electromotive force voltage spike) is significantly longer when probe P is present as compared to when probe P is not present. The effect of a voltage spike and decay is well-established in R-L-C circuits, but the inventors found it surprising that the decay behavior would be measurably affected by the presence of probe shaft S within the core passageway of electromagnetic coil 16 because the probe shaft diameter is very small relative to the internal diameter of coil 16 and there is a significant air gap between the probe shaft and the coil. As alluded to above, the effect is normally obscured by the amplification circuitry used for monitoring voltage induced in coil 16 by motion of probe P during a test subject measurement cycle. The circuitry and processing electronics need to be fast enough to capture this phenomenon, which occurs in about 0.4 milliseconds. By contrast, the probe flight signal during a test subject measurement cycle is one-hundred times slower, taking about 40 milliseconds to complete.

The decay behavior of the counter-electromotive force voltage spike detected in step 106 is evaluated in step 108. In one embodiment, evaluating the decay behavior of the counter-electromotive force voltage spike may include calculating a decay score corresponding to a summation of sampled signal amplitudes of the counter-electromotive force voltage spike acquired over a predetermined period of time. For example, with reference to FIG. 6, the twenty-five "PROBE PRESENT #1" sampled voltage amplitudes added together total 81,300 counts (the decay score when a probe is present), whereas the twenty-five "PROBE NOT PRESENT" sampled voltage amplitudes added together total 60,950 counts (the decay score when no probe is present).

In another embodiment, evaluating the decay behavior of the counter-electromotive force voltage spike may include measuring a decay time of the counter-electromotive force voltage spike. For example, a time period required for the amplitude of the counter-electromotive force voltage spike to decrease to a predetermined level after reaching a peak level associated with saturation may be calculated from the sampled voltage data. With reference to FIG. 6, the "PROBE PRESENT #1" voltage amplitude drops to 2,000 counts after about 0.54 milliseconds and the "PROBE PRESENT #2" voltage amplitude approaches 2,000 counts after about 0.65 milliseconds, whereas the "PROBE NOT PRESENT" voltage amplitude drops to 2,000 counts after only about 0.24 milliseconds.

After the decay behavior of the counter-electromotive force voltage spike is evaluated in step 108, it is correlated to presence or absence of the measurement probe at the measurement launch position pursuant to step 110. Step 110 is a decision block directing flow depending on evaluation of the decay behavior of the counter-electromotive force voltage spike performed in step 108. In the embodiment described above in which a decay score is assigned to the counter-electromotive force voltage spike, a predetermined decay score threshold may be established and stored in memory for use in correlating the decay behavior represented by the decay score to presence or absence of the measurement probe at the measurement launch position. For example, instrument 10 may be calibrated during factory setup by measuring a large set of decay scores with a probe present and another large set of decay scores without a probe present, calculating an average of the decay scores residing between the two sets, and storing the average decay score in instrument memory as a predetermined decay score threshold. For example, calibration of instrument 10 might establish a predetermined decay score threshold of 71,050 counts. The decay behavior of the counter-electromotive force voltage spike may be correlated to presence of the measurement probe at the measurement launch position when the decay score is greater than the predetermined decay score threshold. Conversely, the decay behavior of the counter-electromotive force voltage spike may be correlated to absence of the measurement probe at the measurement launch position when the decay score is less than or equal to the predetermined decay score threshold.

In the embodiment described above in which a decay time of the counter-electromotive force voltage spike is measured, a predetermined decay time threshold may be established and stored in memory for use in correlating the decay behavior represented by the decay time to presence or absence of the measurement probe at the measurement launch position. For example, instrument 10 may be calibrated during factory setup by measuring a large set of decay times with a probe present and another large set of decay times without a probe present, calculating an average of the decay times residing between the two sets, and storing the average decay time in instrument memory as a predetermined decay time threshold. For example, calibration of instrument 10 might establish a predetermined decay time threshold of 0.35 milliseconds. The decay behavior of the counter-electromotive force voltage spike may be correlated to presence of the measurement probe at the measurement launch position when the decay time is greater than the predetermined decay time threshold. Conversely, the decay behavior of the counter-electromotive force voltage spike may be correlated to absence of the measurement probe at the measurement launch position when the decay time is less than or equal to the predetermined decay time threshold.

Thus, as an outcome of step 110, a determination is made as to whether or not a probe P is loaded in instrument 10 in preparation for an ophthalmic measurement, and process flow is directed depending on the determination.

If it is determined that a probe P is present, then method 100 may proceed from decision block 110 along branch Y to step 112 in which the measurement system of instrument 10 is enabled for performing an ophthalmic measurement on a test subject. If method 100 determines that a probe is present, then the voltage supply connectable to rear coil 16 may be switched from the probe detection voltage (first voltage source 40) to the measurement voltage (second voltage source 42), and rear coil 16 may be energized by connecting it to the second voltage source 42 to retain the probe at a launch position while instrument 10 is positioned relative to the test subject for an ophthalmic measurement cycle. These steps may be performed as part of measurement system enablement step 112.

If, however, it is determined that a probe P is not present, then method 100 may proceed from decision block 110 along branch N to step 114 to display an error message, for example a message telling the operator that a probe must be loaded.

In an alternative optional embodiment made possible by the present disclosure, probe detection method 100 may include process steps shared with a normal measurement cycle of instrument 10. If the detection method reaches step 112, an ophthalmic measurement cycle may be commenced in step 116 by energizing front coil 18 to launch measurement probe P toward the eye, and monitoring voltage across rear coil 16 according to step 118 to detect a corresponding voltage signal that may be induced in rear coil 16 by movement of the probe. In the optional embodiment, probe detection method 100 may include a decision block 120 that directs flow depending on whether or not probe motion is indicated. If a voltage spike indicating movement of the probe P is detected, then the probe is not stuck or jammed in place and the measurement cycle will continue according to normal flow. If, however, a voltage spike indicating movement of the probe P is not detected, then the probe is present but is stuck or jammed in place. This information is useful for the operator in conducting the measurement process, but is not available using known probe detection methods. If it is determined that probe P is stuck, then method 100 may proceed along branch N to step 122 to display an error message to the operator, for example a message telling the operator that the probe is jammed.

As will be appreciated from the foregoing description, the present disclosure improves the state of the art by providing an energy efficient approach for detecting presence or absence of a measurement probe, and making it possible to check if a detected probe is stuck or jammed in the ophthalmic instrument. The disclosed probe detection method does not interfere with normal operation of the instrument to measure ophthalmic parameters.

What is claimed is:

1. A method of detecting presence or absence of a measurement probe at a measurement launch position in an ophthalmic instrument, the measurement probe comprising a magnetic shaft, the ophthalmic instrument comprising an electromagnetic coil defining a core passageway for receiving at least a portion of the magnetic shaft when the magnetic shaft is at the measurement launch position, the method comprising the steps of:
   applying a temporary current pulse to the electromagnetic coil;
   detecting a counter-electromotive force voltage spike induced in the electromagnetic coil by the current pulse;
   evaluating a decay behavior of the counter-electromotive force voltage spike; and
   correlating the decay behavior of the counter-electromotive force voltage spike to presence or absence of the measurement probe at the measurement launch position.

2. The method according to claim 1, wherein:
   evaluating the decay behavior of the counter-electromotive force voltage spike includes calculating a decay score corresponding to a summation of sampled signal amplitudes of the counter-electromotive force voltage spike acquired over a predetermined period of time;
   the decay behavior of the counter-electromotive force voltage spike is correlated to presence of the measurement probe at the measurement launch position when the decay score is greater than a predetermined decay score threshold; and
   the decay behavior of the counter-electromotive force voltage spike is correlated to absence of the measurement probe at the measurement launch position when the decay score is less than or equal to the predetermined decay score threshold.

3. The method according to claim 2, wherein the predetermined decay score threshold is a stored parameter determined during calibration of the ophthalmic instrument.

4. The method according to claim 1, wherein:
   evaluating the decay behavior of the counter-electromotive force voltage spike includes measuring a decay time of the counter-electromotive force voltage spike;
   the measured decay time is correlated to presence of the measurement probe at the measurement launch position when the decay time is greater than a predetermined decay time threshold; and
   the measured decay time is correlated to absence of the measurement probe at the measurement launch position when the decay time is less than or equal to the predetermined decay time threshold.

5. The method according to claim 4, wherein the predetermined decay time threshold is a stored parameter determined during calibration of the ophthalmic instrument.

6. The method according to claim 1, further comprising the step of energizing the electromagnetic coil, after the step of detecting the counter-electromotive force voltage spike, to retain the measurement probe at the measurement launch position if the measurement probe is present at the measurement launch position.

7. The method according to claim 6, wherein:
   the step of applying the temporary current pulse to the electromagnetic coil includes connecting a first voltage to the electromagnetic coil; and
   the step of energizing the electromagnetic coil to retain the measurement probe includes connecting a second voltage to the electromagnetic coil;
   wherein the second voltage is greater than the first voltage.

8. The method according to claim 1, wherein the current pulse is applied to the electromagnetic coil for a time duration in a range from 1 millisecond through 3 milliseconds.

9. The method according to claim 1, wherein the ophthalmic instrument includes a second electromagnetic coil arranged to propel the measurement probe away from the measurement launch position when the second electromagnetic coil is energized, and wherein the method further comprises:
   energizing the second electromagnetic coil in response to correlation of the decay behavior of the counter-electromotive force voltage spike to presence of the measurement probe at the launch position;
   monitoring voltage across the electromagnetic coil to detect a corresponding motion voltage signal induced in the electromagnetic coil by expected movement of the measurement probe; and
   displaying an error message if the motion voltage signal is not detected.

10. An ophthalmic instrument comprising:
    an electromagnetic coil defining a core passageway;
    drive electronics configured to connect a first voltage to the electromagnetic coil to apply a temporary current pulse in the electromagnetic coil;
    measurement electronics configured to detect a counter-electromotive force voltage spike induced in the electromagnetic coil by the current pulse and generate a probe detection signal representing the counter-electromotive force voltage spike; and processing electronics configured to evaluate a decay behavior of the counter-electromotive force voltage spike and correlate the decay behavior of the counter-electromotive force voltage spike to presence or absence of a disposable measurement probe at a measurement launch position within the core passageway.

11. The ophthalmic instrument according to claim 10, wherein:

the processing electronics is configured to evaluate the decay behavior of the counter-electromotive force voltage spike by calculating a decay score corresponding to a summation of sampled signal amplitudes of the counter-electromotive force voltage spike acquired over a predetermined period of time;

the processing electronics is configured to correlate the decay behavior of the counter-electromotive force voltage spike to presence of the measurement probe at the measurement launch position when the decay score is greater than a predetermined decay score threshold; and the processing electronics is configured to correlate the decay behavior of the counter-electromotive force voltage spike to absence of the measurement probe at the measurement launch position when the decay score is less than or equal to the predetermined decay score threshold.

12. The ophthalmic instrument according to claim 11, wherein the predetermined decay score threshold is determined during calibration of the ophthalmic instrument and stored in a memory associated with the processing electronics.

13. The ophthalmic instrument according to claim 10, wherein:

the processing electronics is configured to evaluate the decay behavior of the counter-electromotive force voltage spike by measuring a decay time of the counter-electromotive force voltage spike;

the processing electronics is configured to correlate the decay behavior of the counter-electromotive force voltage spike to presence of the measurement probe at the measurement launch position when the decay time is greater than a predetermined decay time threshold; and the processing electronics is configured to correlate the decay behavior of the counter-electromotive force voltage spike to absence of the measurement probe at the measurement launch position when the decay time is less than or equal to the predetermined decay time threshold.

14. The ophthalmic instrument according to claim 13, wherein the predetermined decay time threshold is determined during calibration of the ophthalmic instrument and stored in a memory associated with the processing electronics.

15. The ophthalmic instrument according to claim 10, wherein the drive electronics is further configured to energize the electromagnetic coil to retain the measurement probe at the measurement launch position if the measurement probe is present at the measurement launch position.

16. The ophthalmic instrument according to claim 15, wherein:

the drive electronics is configured to connect a second voltage to the electromagnetic coil to energize the electromagnetic coil to retain the measurement probe at the measurement launch position; and the second voltage is greater than the first voltage.

17. The ophthalmic instrument according to claim 10, wherein the drive electronics is configured to connect the first voltage to the electromagnetic coil for a time duration in a range from 1 millisecond through 3 milliseconds.

18. The ophthalmic instrument according to claim 10, wherein the ophthalmic instrument comprises a rebound tonometer for measuring intraocular pressure.

* * * * *